(12) United States Patent
Karam

(10) Patent No.: US 11,992,346 B2
(45) Date of Patent: May 28, 2024

(54) COMPUTER READABLE STORAGE MEDIA FOR REMOTE PATIENT MANAGEMENT AND METHODS AND SYSTEMS FOR UTILIZING SAME

(71) Applicant: Optum, Inc., Minnetonka, MN (US)

(72) Inventor: Houssam Karam, Imlay City, MI (US)

(73) Assignee: Optum, Inc., Minnetonka, MN (US)

(*) Notice: Subject to any disclaimer, the term of this patent is extended or adjusted under 35 U.S.C. 154(b) by 1451 days.

(21) Appl. No.: 14/568,593

(22) Filed: Dec. 12, 2014

(65) Prior Publication Data

US 2016/0171168 A1 Jun. 16, 2016

(51) Int. Cl.
| | | |
|---|---|---|
| A61B 5/00 | (2006.01) | |
| A61B 5/01 | (2006.01) | |
| A61B 5/021 | (2006.01) | |
| A61B 5/024 | (2006.01) | |
| A61B 5/145 | (2006.01) | |
| G16H 40/67 | (2018.01) | |

(52) U.S. Cl.
CPC ............ *A61B 5/742* (2013.01); *A61B 5/0022* (2013.01); *G16H 40/67* (2018.01); *A61B 5/01* (2013.01); *A61B 5/021* (2013.01); *A61B 5/024* (2013.01); *A61B 5/14532* (2013.01); *A61B 5/14542* (2013.01); *A61B 2562/08* (2013.01)

(58) Field of Classification Search
CPC ............... G06F 19/3418; A61B 5/0022; A61B 1/00–2576/026; G16H 10/00–80/00
See application file for complete search history.

(56) References Cited

U.S. PATENT DOCUMENTS

| | | | |
|---|---|---|---|
| 6,612,985 B2 | 9/2003 | Eiffert et al. | |
| 8,682,952 B2 | 3/2014 | Kutzik et al. | |
| 8,882,666 B1* | 11/2014 | Goldberg | A61B 5/02 600/301 |
| 2002/0013517 A1* | 1/2002 | West | A61B 5/1113 600/300 |

(Continued)

OTHER PUBLICATIONS

Jara et al., "Interconnection Framework for mHealth and Remote Monitoring Based on the Internet of Things," IEEE Journal On Selected Areas in Communications/Supplement, vol. 31, No. 9, Sep. 2013 47; Digital Object Identifier 10.1109/JSAC.2013.SUP. 0513005. (Year: 2013).*

*Primary Examiner* — Jonathon A. Szumny
(74) *Attorney, Agent, or Firm* — Alston & Bird LLP

(57) ABSTRACT

Remote patient management involves receiving an enrollment request to enroll a patient, identification of vitals of the patient to be measured based on the enrollment request, providing an equipment request indicating the vitals of the patient to be measured, receiving equipment information corresponding to one or more health measurement devices for measuring the vitals of the patient, and associating the patient with the equipment information corresponding to the one or more health measurement devices. In addition, a user device establishes communication with a health measurement device and determines whether it is associated with the patient, and if so, receives measurements from the health measurement device and provides the measurements to a healthcare management server. Otherwise, if not associated with the patient, no measurements are received from the health measurement device.

10 Claims, 25 Drawing Sheets

(56) References Cited

U.S. PATENT DOCUMENTS

| | | | | |
|---|---|---|---|---|
| 2005/0197545 | A1* | 9/2005 | Hoggle | G16H 40/67 128/923 |
| 2007/0033072 | A1* | 2/2007 | Bildirici | G06F 19/3418 705/3 |
| 2011/0077956 | A1* | 3/2011 | Kapu | G06F 19/3418 705/2 |
| 2011/0161110 | A1* | 6/2011 | Mault | G06Q 30/02 705/3 |
| 2011/0307274 | A1* | 12/2011 | Thompson | G06Q 10/06311 705/3 |
| 2012/0030229 | A1* | 2/2012 | Ji | G06F 19/322 707/769 |
| 2012/0203566 | A1* | 8/2012 | Kidd | G06Q 50/22 705/2 |
| 2013/0018668 | A1* | 1/2013 | Goldberg | G06Q 40/08 705/2 |
| 2013/0086122 | A1* | 4/2013 | Devenyi | G06F 19/3418 707/797 |
| 2013/0095459 | A1* | 4/2013 | Tran | A61B 5/6816 434/247 |
| 2013/0226604 | A1* | 8/2013 | Etchegoyen | G06Q 50/22 705/2 |
| 2013/0311104 | A1* | 11/2013 | Inoue | G06F 19/3418 702/19 |
| 2014/0276104 | A1* | 9/2014 | Tao | A61B 5/7239 600/476 |
| 2014/0278475 | A1* | 9/2014 | Tran | G06F 19/3418 705/2 |
| 2015/0025329 | A1* | 1/2015 | Amarasingham | G06F 19/3456 600/301 |
| 2015/0142367 | A1* | 5/2015 | Yurach | G16H 10/40 702/123 |
| 2015/0154367 | A1* | 6/2015 | Shetty | G16H 50/20 705/2 |
| 2017/0331524 | A1* | 11/2017 | Aranyosi | H04B 5/0075 |

* cited by examiner

| | | | | 1006 | 1008 | | | 1002 | |
|---|---|---|---|---|---|---|---|---|---|

500

| COMPANY NAME | | DASHBOARD | PATIENT LIST | ADD MEMBER | | | | CHRIS JAMES ▼ | |
|---|---|---|---|---|---|---|---|---|---|
| NEW READINGS (100) | HAVE NOT TESTED (40) | ON HOLD AND HA...(10) | | RECENTLY ACKNOWLEDGED (24) | | SUSPENDED (12) | | | |
| ▼ | 🔍 ENTER PATIENT NAME | SHOWING 1 TO 20 OF 100 PATIENTS | | | PER PAGE 20 ▼ | ◄ PAGE 1 OF 5 ► | | ⚙ | |
| ⊞ | DIVISION | PATIENT NAME | DATE & TIME | WEIGHT-LBS | BP-MMHG | HR-BPM | SPO2-% | TEMP-F | Q&A |
| ⊟ | NORTH WEST | ⓘ PATIENT 1 | TODAY 11:05 AM | 126.0 | 128/73 | 80 | 88 ✉ | 98.6 | 0/5 | 📋 |
| | 1012 | | TODAY 10:30 AM | 119.0 | 139/72 | 47 ✉ | 98 | 101.2 | 1/5 | 📋 1011 |
| | | | TODAY 9:38 AM | 126.0-P ✉ | 125/75 | 70 | 96 | 98.6 | 0/5 | 📋 |
| | LONG DIVISO. | ⓘ PATIENT 2 | TODAY 9:00 AM | 159.5 | 137/67 | 54 | 95 | 100.2 | 1/5 | 📋 |
| ⊞ | NORTH WEST | ⓘ PATIENT 3 | TODAY 9:00 AM | 294.0 | 182/100-P | 88 | 94 | 98.6 | 0/5 | 📋 1010 |
| | SOUTH WEST | ⓘ PATIENT 4 | YESTERDAY 11:05 AM | 128.0 | 129/66 | 121 | 94 | 98.6 | 0/5 | 📋 |
| | NORTH WEST | ⓘ PATIENT 5 | YESTERDAY 11:05 AM | 186.0 | 142/60 | 88 | 91 | 98.6 | 0/5 | 📋 |
| ⊞ | SOUTH WEST | ⓘ PATIENT 6 | YESTERDAY 11:05 AM | 131.0 ✉ | 129/66 | 78 | 99 | 98.6 | 0/5 | 📋 |
| ⊞ | NORTH WEST | ⓘ PATIENT 7 | YESTERDAY 11:05 AM | 166.0 | 170/80 | 90 | 90 | 98.6 | 0/5 | 📋 |
| | SOUTH WEST | ⓘ PATIENT 8 | YESTERDAY 11:05 AM | 198.0 | 142/60 | 67 | 96 | 98.6 | 0/5 | 📋 |
| | SOUTH WEST | ⓘ PATIENT 9 | TODAY 11:05 AM | 187.0-? | 182/90-? | 110-? | 97-? | 100.8-? | ?/5 | 📋 |
| ⊞ | SOUTH WEST | ⓘ PATIENT 10 | TODAY 11:05 AM | 220.0-? | 152/90-? | 90-? | 80-? | 98.6-? | ?/5 | 📋 |
| | NORTH WEST | ⓘ PATIENT 11 | YESTERDAY 11:05 AM | -- | --/-- | -- | -- | -- | -- | 📋 |
| | SOUTH WEST | ⓘ PATIENT 12 | YESTERDAY 11:05 AM | -- | --/-- | -- | -- | -- | -- | 📋 |
| ⊞ | SOUTH WEST | ⓘ PATIENT 13 | 01/27/14 10:45 AM | 186.0 | 139/72 | 88 | 98 | 98.6 | 0/5 | 📋 |
| | NORTH WEST | ⓘ PATIENT 14 | 01/27/14 10:45 AM | 171.0 | 125/75 | 78 | 96 | 98.6 | 0/5 | 📋 |
| | SOUTH WEST | ⓘ PATIENT 15 | 01/05/14 7:00 AM | 142.6 | 142/60 | 90 | 98 | 98.6 | 0/5 | 📋 |
| ⊞ | NORTH WEST | ⓘ PATIENT 16 | TODAY 11:05 AM | 112.2 | 137/67 | 67 | 99 | 98.6 | 0/5 | 📋 |
| ⊞ | SOUTH WEST | ⓘ PATIENT 17 | TODAY 11:05 AM | 190.0 | 125/75 | 88 | 98 | 98.6 | 0/5 | 📋 |
| | SOUTH WEST | ⓘ PATIENT N | TODAY 11:05 AM | 230.0 | 125/75 | 78 | 95 | 98.6 | 0/5 | 📋 |
| | | | | | | | ◄ PAGE 1 OF 5 ► | BACK TO TOP | |

| | COMPANY NAME | | | DASHBOARD | PATIENT LIST | ADD MEMBER | | | CHRIS JAMES ▼ |
|---|---|---|---|---|---|---|---|---|---|
| | NEW READINGS (100) | | HAVE NOT TESTED (40) | ON HOLD AND HA...(10) | RECENTLY ACKNOWLEDGED (24) | | SUSPENDED (12) | | |
| ▼ | 🔍 ENTER PATIENT NAME | | SHOWING 1 TO 20 OF 100 PATIENTS | | | PER PAGE 20 ▼ | ‹ PAGE 1 OF 5 › | | ⚙ |
| ± | DIVISION | PATIENT NAME | DATE & TIME | WEIGHT-LBS | BP-MMHG | HR-BPM | SPO2-% | TEMP-F | Q&A |
| ⊟ | NORTH WEST | ⓘ PATIENT 1 | TODAY 11:05 AM | 126.0 | 128/73 | 80 | 88 📈 | 98.6 | 0/5 |
| | | | TODAY 10:30 AM | | ❤ BLOOD PRESSURE ✎ X | | 98 | 101.2 | 1/5 |
| | | | TODAY 9:38 AM | 12 | SYSTOLIC 100-160 MMHG | | 96 | 98.6 | 0/5 |
| | SOUTH EAST | ⓘ PATIENT 2 | TODAY 9:00 AM | | DIASTOLIC 40-75 MMHG | | 95 | 100.2 | 1/5 |
| ± | NORTH WEST | ⓘ PATIENT 3 | TODAY 9:00 AM | 294.0 | 182/100 - P | 88 | 94 | 98.6 | 0/5 |
| | SOUTH WEST | ⓘ PATIENT 4 | YESTERDAY 11:05 AM | 128.0 | 129/66 | 121 | 94 | 98.6 | 0/5 |
| | NORTH WEST | ⓘ PATIENT 5 | YESTERDAY 11:05 AM | 186.0 | 142/60 | 88 | 91 | 98.6 | 0/5 |
| ± | SOUTH WEST | ⓘ PATIENT 6 | YESTERDAY 11:05 AM | 131.0 📈 | 129/66 | 78 | 99 | 98.6 | 0/5 |
| ± | NORTH WEST | ⓘ PATIENT 7 | YESTERDAY 11:05 AM | 186.0 | 170/80 | 90 | 90 | 98.6 | 0/5 |
| | SOUTH WEST | ⓘ PATIENT 8 | YESTERDAY 11:05 AM | 198.0 | 142/60 | 67 | 96 | 98.6 | 0/5 |
| | SOUTH WEST | ⓘ PATIENT 9 | TODAY 11:05 AM | 187.0-? | 182/90-? | 110-? | 97-? | 100.8-? | ?/5 |
| ± | SOUTH WEST | ⓘ PATIENT 10 | TODAY 11:05 AM | 220.0-? | 152/90-? | 90-? | 80-? | 98.6-? | ?/5 |
| ± | NORTH WEST | ⓘ PATIENT 11 | YESTERDAY 11:05 AM | -- | --/-- | -- | -- | -- | -- |
| | SOUTH WEST | ⓘ PATIENT 12 | YESTERDAY 11:05 AM | -- | --/-- | -- | -- | -- | -- |
| | SOUTH WEST | ⓘ PATIENT 13 | 01/27/14 10:45 AM | 186.0 | 139/72 | 88 | 98 | 98.6 | 0/5 |
| ± | NORTH WEST | ⓘ PATIENT 14 | 01/27/14 10:45 AM | 171.0 | 125/75 | 78 | 96 | 98.6 | 0/5 |
| | SOUTH WEST | ⓘ PATIENT 15 | 01/05/14 7:00 AM | 142.6 | 142/60 | 90 | 98 | 98.6 | 0/5 |
| ± | NORTH WEST | ⓘ PATIENT 16 | TODAY 11:05 AM | 112.2 | 137/67 | 67 | 99 | 98.6 | 0/5 |
| ± | SOUTH WEST | ⓘ PATIENT 17 | TODAY 11:05 AM | 190.0 | 125/75 | 88 | 98 | 98.6 | 0/5 |
| | SOUTH WEST | ⓘ PATIENT-N | TODAY 11:05 AM | 230.0 | 125/75 | 78 | 95 | 98.6 | 0/5 |

‹ PAGE 1 OF 5 › ▸ BACK TO TOP

| | | | | | | | | | |
|---|---|---|---|---|---|---|---|---|---|
| COMPANY NAME | | | DASHBOARD | PATIENT LIST | ADD MEMBER | | | CHRIS JAMES ▾ | |
| NEW READINGS (100) | | HAVE NOT TESTED (40) | ON HOLD AND HA...(10) | | RECENTLY ACKNOWLEDGED (24) | | SUSPENDED (12) | | |
| ▼ | ENTER PATIENT NAME | SHOWING 1 TO 20 OF 100 PATIENTS | | | PER PAGE 20 ▾ | ◂ PAGE 1 OF 5 ▸ | | ✱ | |
| ⊞ | DIVISION | PATIENT NAME | DATE & TIME | WEIGHT-LBS | BP-MMHG | HR-BPM | SPO2-% | TEMP-F | Q&A |
| ⊟ | NORTH WEST | PATIENT 1 | TODAY 11:05 AM | 126.0 | 128/73 | 80 | 88 ✉ | 98.6 | 0/5 |
| | | | TODAY 10:30 AM | 119.0 | 139/72 | 47 ✉ | 98 | 101.2 | 1/5 |
| | | | | | | | | | 0/5 |
| | SOUTH EAST | PATIENT 2 | | | | | | | 1/5 |
| ⊞ | NORTH WEST | PATIENT 3 | | | | | | | 0/5 |
| | SOUTH WEST | PATIENT 4 | | | | | | | 0/5 |
| | NORTH WEST | PATIENT 5 | | | | | | | 0/5 |
| ⊞ | SOUTH WEST | PATIENT 6 | | | | | | | 0/5 |
| ⊞ | NORTH WEST | PATIENT 7 | | | | | | | 0/5 |
| | SOUTH WEST | PATIENT 8 | | | | | | | 0/5 |
| | SOUTH WEST | PATIENT 9 | | | | | | | ?/5 |
| ⊞ | SOUTH WEST | PATIENT 10 | TODAY 11:05 AM | 220.0-? | 152/90-? | 90-? | 80-? | 98.6-? | ?/5 |
| ⊞ | NORTH WEST | PATIENT 11 | YESTERDAY 11:05 AM | -- | --/-- | -- | -- | -- | -- |
| | SOUTH WEST | PATIENT 12 | YESTERDAY 11:05 AM | -- | --/-- | -- | -- | -- | -- |
| | SOUTH WEST | PATIENT 13 | 01/27/14 10:45 AM | 186.0 | 139/72 | 88 | 98 | 98.6 | 0/5 |
| ⊞ | NORTH WEST | PATIENT 14 | 01/27/14 10:45 AM | 171.0 | 125/75 | 78 | 96 | 98.6 | 0/5 |
| | SOUTH WEST | PATIENT 15 | 01/05/14 7:00 AM | 142.6 | 142/60 | 90 | 98 | 98.6 | 0/5 |
| ⊞ | NORTH WEST | PATIENT 16 | TODAY 11:05 AM | 112.2 | 137/67 | 67 | 99 | 98.6 | 0/5 |
| ⊞ | SOUTH WEST | PATIENT 17 | TODAY 11:05 AM | 190.0 | 125/75 | 88 | 98 | 98.6 | 0/5 |
| | SOUTH WEST | PATIENT-N | TODAY 11:05 AM | 230.0 | 125/75 | 78 | 95 | 98.6 | 0/5 |

Q&A popup (1022, 1024):
1 CAUTIONARY ANSWER OF 5
Q4 ARE YOU ABLE TO EAT AND DRINK NORMALLY? — NO
Q1 M IPSUM DOLOR SIT AMET, CONSECTETUR ADIPISICING ELIT, SED DO EIUSMOD TEMPOR INCIDIDUN? — YES
Q2 IPSUM DOLOR SIT AMET, CONSECTETUR ADIPISICING ELIT, SED DO EIUSMOD TEMPOR INCIDIDUN? — YES
Q3 IPSUM DOLOR SIT AMET, CONSECTETUR ADIPISICING ELIT, SED DO EIUSMOD TEMPOR INCIDIDUN CONSECTETUR ADIPISICING ELIT, SED DO EIUSMOD TEMPOR INCIDIDUN CONSECTETUR ADIPISICING ELIT, SED DO EIUSMOD TEMPOR INCIDIDUNCONSECTETUR ADIPISICING ELIT, SED DO EIUSMOD — YES

◂ PAGE 1 OF 5 ▸ BACK TO TOP

| COMPANY NAME | | | DASHBOARD | PATIENT LIST | ADD MEMBER | | CHRIS JAMES ▼ |
|---|---|---|---|---|---|---|---|
| ↑↓ ▼ | ENTER PATIENT NAME | SHOWING 1 TO 20 OF 100 PATIENTS | | | PER PAGE 20 | ‹ PAGE 1 OF 5 › | ✱ |
| DIVISION | PATIENT NAME | MEDICAL ID | CARE PROVIDER | INSURANCE- ID # | LAST SPOKEN TO | STATUS | |
| NORTH WEST | ⓘ WATSON, MARY | 463942 | TRAN, RYAN | UHC-987698708080 | TODAY 11:05 AM | ACTIVE | |
| SOUTH EAST | ⓘ PATIENT 1... | 1080952 | PROVIDER NAME LONG. | UHC-7869809886586 | TODAY 10:30 AM | SUSPENDED 🔒 | |
| NORTH WEST | ⓘ PATIENT 2 | 91862980 | TRAN, RYAN | BCBS-91862980 | TODAY 9:38 AM | ACTIVE | |
| SOUTH EAST | ⓘ PATIENT 3 | 96812858 | PROVIDER NAME | UHC-96812858 | TODAY 9:00 AM | ACTIVE | |
| NORTH WEST | ⓘ PATIENT 4 | HOME HEALTH CARE | PROVIDER NAME | UHC-3129869860 | TODAY 9:00 AM | ACTIVE | |
| SOUTH WEST | ⓘ PATIENT 5 | 676567899 | PROVIDER NAME | BCBS-676567899 | YESTERDAY 11:05 AM | ACTIVE | |
| NORTH WEST | ⓘ PATIENT 6 | 96812858 | PROVIDER NAME | UHC-96812858 | YESTERDAY 11:05 AM | ACTIVE | |
| SOUTH WEST | ⓘ PATIENT 7 | HOME HEALTH CARE | PROVIDER NAME | HUMANA-7945649 | YESTERDAY 11:05 AM | ACTIVE | |
| NORTH WEST | ⓘ PATIENT 8 | HOME HEALTH CARE | PROVIDER NAME | UHC-096874575237659 | YESTERDAY 11:05 AM | ACTIVE | |
| SOUTH WEST | ⓘ PATIENT 9 | 24233456133 | PROVIDER NAME | AETNA-24233456133 | YESTERDAY 11:05 AM | ACTIVE | |
| SOUTH WEST | ⓘ PATIENT 10 | 96812858 | PROVIDER NAME | UHC-96812858 | TODAY 11:05 AM | ACTIVE | |
| SOUTH WEST | ⓘ PATIENT 11 | 24637645711 | PROVIDER NAME | BCBS-24637645711 | TODAY 11:05 AM | ACTIVE | |
| NORTH WEST | ⓘ PATIENT 12 | 87576475438 | PROVIDER NAME | UHC-87576475438 | YESTERDAY 11:05 AM | ACTIVE | |
| SOUTH WEST | ⓘ PATIENT 13 | HOME HEALTH CARE | PROVIDER NAME | UHC-4979609775688 | YESTERDAY 11:05 AM | ACTIVE | |
| SOUTH WEST | ⓘ PATIENT 14 | 96812858 | PROVIDER NAME | HUMANA-96812858 | 01/27/14 10:45 AM | SUSPENDED 🔒 | |
| NORTH WEST | ⓘ PATIENT 15 | 17646578886 | PROVIDER NAME | UHC-17646578886 | 01/27/14 10:45 AM | ACTIVE | |
| SOUTH WEST | ⓘ PATIENT 16 | HOME HEALTH CARE | PROVIDER NAME | BCBS-76546980085 | 01/05/14 7:00 AM | SUSPENDED 🔒 | |
| NORTH WEST | ⓘ PATIENT 17 | 96812858 | PROVIDER NAME | UHC- 96812858 | TODAY 11:05 AM | SUSPENDED 🔒 | |
| SOUTH WEST | ⓘ PATIENT 18 | 097574764 | PROVIDER NAME | UHC-097574764 | TODAY 11:05 AM | ACTIVE | |
| SOUTH WEST | ⓘ PATIENT N | 96812858 | PROVIDER NAME | HUMANA-96812858 | TODAY 11:05 AM | SUSPENDED 🔒 | |
| | | | | | ‹ PAGE 1 OF 30 › | BACK TO TOP | |

| COMPANY NAME | | | DASHBOARD | PATIENT LIST | ADD MEMBER | | CHRIS JAMES ▼ |
|---|---|---|---|---|---|---|---|

| ↑↓ ▼ | 🔍 ENTER PATIENT NAME | SHOWING 1 TO 20 OF 700 PATIENTS | PER PAGE [20 ▼] ◀ PAGE [1] OF [30] ▶ ⚙ |
|---|---|---|---|

SELECT FILTERS

| DIVISION | INSURANCE | | X |
|---|---|---|---|
| ☐ ALL<br>☐ NORTH WEST<br>☐ SOUTH WEST<br>☐ NORTH EAST<br>☐ SOUTH EAST | ☐ ALL<br>☐ OPTUM<br>☐ UNITED HEALTH GROUP<br>☐ BLUE CROSS BLUE SHIELD<br>☐ HAP | ☐ ACTIVE<br>☐ SUSPENDED | |

☐ CLEAR ALL                                                                                   CANCEL [ APPLY ]

| DIVISION | PATIENT NAME | MEDICAL ID | CARE PROVIDER | INSURANCE- ID # | LAST SPOKEN TO | STATUS |
|---|---|---|---|---|---|---|
| NORTH WEST ⓘ | WATSON, MARY | 463942 | TRAN, RYAN | UHC-987698708080 | TODAY 11:05 AM | ACTIVE |
| SOUTH EAST ⓘ | PATIENT 1... | 1080952 | PROVIDER NAME LONG... | UHC-7869809886586 | TODAY 10:30 AM | SUSPENDED 🔒 |
| NORTH WEST ⓘ | PATIENT 2 | 91862980 | TRAN, RYAN | BCBS-91862980 | TODAY 9:38 AM | ACTIVE |
| NORTH WEST ⓘ | PATIENT 3 | 96812858 | PROVIDER NAME | UHC-96812858 | TODAY 9:00 AM | ACTIVE |
| NORTH WEST ⓘ | PATIENT 4 | HOME HEALTH CARE | PROVIDER NAME | UHC-... | | |

| | | | | | | | |
|---|---|---|---|---|---|---|---|
| COMPANY NAME | | | DASHBOARD | PATIENT LIST | ADD MEMBER | | CHRIS JAMES ▼ |

MARY WATSON (734) 709-5788

| PATIENT INFORMATION (INCOMPLETE) | MEDICATIONS | CLINICAL ORDERS | ACCOUNT HISTORY | ALERT HISTORY | PATIENT MANAGEMENT | PATIENT ASSIGNMENT | ACCOUNT STATUS |
|---|---|---|---|---|---|---|---|

SHOW READINGS FOR [14 DAYS ▼] [12/12/14] TO [2/30/14]     PATIENT DETAILS ‹ PAGE [1] OF [1] ›

| DATE & TIME | WEIGHT-LBS | BP-MMHG | HR-BPM | SPO2-% | TEMP-F | Q&A | NURSE RESPONSES MORE > |
|---|---|---|---|---|---|---|---|
| TODAY 11:05 AM | 171.0 | 128/73 | 80 | 96 | 98.6 | 0/5 | |
| TODAY 10:30 AM | 119.0 | 139/72 | 47 | 98 | 101.2 | 1/5 | |
| TODAY 9:38 AM | 126.0 | 125/75 | 70 | 96* 6 | 98.6 | 0/5 | PUT ON HOLD BY C. JONES AT 11:00 AM TODAY LEFT PATIENT VOICEMAIL, LOREM IPSUM... PATIENT'S WEIGHT DOES NOT LOOK... MORE > |
| TODAY 9:00 AM | 294.0 | 182/100 | 88 | 94 | 98.6 | 0/5 | ACKNOWLEDGED BY C. JONES AT 12:30 PM TODAY SPOKE TO PATIENT, CONTINUE TO MONITOR, LO... PATIENT'S WEIGHT DOES NOT LOOK... MORE > |
| YESTERDAY 11:35 AM | 186.0 | 142/60 | 88 | 91 | 98.6 | 0/5 | ACKNOWLEDGED BY C. JONES AT 12:30 PM TODAY SPOKE TO PATIENT, CONTINUE TO MONITOR... PATIENT TOLD ME READINGS OVER THE PHONE. 180* LBS  PUT ON HOLD BY C. JONES AT 11:00 AM TODAY LEFT PATIENT VOICEMAIL PATIENT'S WEIGHT DOES NOT LOOK RIGHT SO MARKED AS INVALID. 123  161.0 LBS  ✉ RE-TEST WEIGHT ‹ LESS |
| 01/27/14 10:45 AM | 126.0 | 125/75 | 78 | 96 | 98.6 | 0/5 | ACKNOWLEDGED BY C. JONES AT 12:30 PM TODAY SPOKE TO PATIENT, CONTINUE TO MONITOR, LO... PATIENT'S WEIGHT DOES NOT LOOK... MORE > |
| 01/05/14 7:00 AM | 112.2 | 137/67 | 67 | 99 | 98.6 | 0/5 | ACKNOWLEDGED BY C. JONES AT 12:30 PM TODAY SPOKE TO PATIENT, CONTINUE TO MONITOR, LO... PATIENT'S WEIGHT DOES NOT LOOK... MORE > |
| 01/05/14 7:00 AM | 230.0 | 125/75 | 78 | 95 | 98.6 | 0/5 | ACKNOWLEDGED BY C. JONES AT 12:30 PM TODAY SPOKE TO PATIENT, CONTINUE TO MONITOR, LO... PATIENT'S WEIGHT DOES NOT LOOK... MORE > |
| 12/29/13 3:00 PM | 220.0 - ? | 152/90 - ? | 90 - ? | 80 - ? | 98.6 - ? | 0/5 - ? | ACKNOWLEDGED BY C. JONES AT 12:30 PM TODAY |

‹ PAGE [1] OF [1] › BACK TO TOP

| COMPANY NAME | | DASHBOARD  PATIENT LIST  ADD MEMBER | | CHRIS JAMES ▼ |

MARY WATSON  (734) 709-5788

| PATIENT INFORMATION | MEDICATIONS | CLINICAL ORDERS | ACCOUNT HISTORY | ALERT HISTORY | PATIENT MANAGEMENT | PATIENT ASSIGNMENT | ACCOUNT STATUS |

PATIENT INFORMATION  (i) LAST SPOKEN TO BY C. JONES ON 2/28/14 AT 11:05AM.

MRS. MARY ANN WATSON

ENGLISH
FEMALE
DOB: 12/24/1958
HEIGHT: 5'6"
WEIGHT: 160 LBS

CATEGORY: HIGH RISK
DIVISION: NORTH WEST
MEDICAL ID: 463942
DEVICE ID: 54546278

CONTACT
1023 BARTON DR
LAS VEGAS NV 56034
LOREM IPSUM LOREM
BLAH BLAH DESCRIPTION

1023 BARTON DR
LAS VEGAS NV 56034
LOREM IPSUM LOREM
BLAH BLAH DESCRIPTION

+1 734 564 4423 *
+1 734 234 7733

MARYANN@GMAIL.COM

* PRIMARY CONTACT

EMERGENCY CONTACTS
DR. JOHN WATSON (SPOUSE)
+1 734 564 4423*
+1 734 234 7733
JOE WATSON (SON)
+1 734 564 4423*
+1 734 234 7733

CARE PROVIDER
* DR. RYAN TRAN
1023 BARTON DR
LAS VEGAS NV 56034
+1 734 564 4423, +1 734 546 6677
FAX: +1 734 234 7733

DR. RYAN GOSLING
1023 BARTON PL
LAS VEGAS NV 56034
+1 734 564 4423, +1 734 546 6677
FAX: +1 734 234 7733

INSURANCE
* UNITED HEALTH CARE
SERIAL #: 46394287699
1023 BARTON DR
LAS VEGAS NV
+1 734 564 4423, +1 734 676 9988
FAX: +1 734 234 7733

AETNA
SERIAL #: 46394287699
1023 BARTON DR
LAS VEGAS NV 56034
+1 734 564 4423, +1 789 888 6546
FAX: +1 734 234 7733

| COMPANY NAME | | DASHBOARD | PATIENT LIST | ADD MEMBER | | | CHRIS JAMES ▼ |
|---|---|---|---|---|---|---|---|

MARY WATSON (734) 709-5788

CLINICIAN VITALS     X

*DATE [2/12/14]  *TIME [07:00 AM ▼]

☑ HR BPM [ ]  ☐ HR BPM [ ]  ☐ HR BPM [ ]  ☐ HR BPM [ ]  ☐ HR BPM [ ]

ADD COMMENTS [ ]

*REQUIRED     1063     CANCEL    ADD

SHOW READINGS FOR [14 DAYS ▼] [2/12/14] TO [2/30/14]     PER PAGE [ALL ▼] ◂ PAGE [1] OF [1] ▸

| DATE & TIME | WEIGHT-LBS | BP- MMHG | HR- BPM | SPO2- % | TEMP- F | Q&A | NURSE RESPONSES | MORE > |
|---|---|---|---|---|---|---|---|---|
| TODAY 11:05 AM | 171.0 | 128/73 | 80 | 96 | 98.6 | 0/5 | 📋 | |
| TODAY 10:30 AM | 119.0 | 139/72 | 47 | 98 | 101.2 | 1/5 | 📋 | |
| TODAY 9:38 AM | 126.0 📈 | 125/75 | 70 | 96* 6 | 98.6 | 0/5 | 📋 | PUT ON HOLD BY C. JONES AT 11:00 AM TODAY LEFT PATIENT VOICEMAIL. LOREM IPSUM... PATIENT'S WEIGHT DOES NOT LOOK... MORE > |
| TODAY 9:00 AM | 294.0 | 182/100 | 88 | 94 | 98.6 | 0/5 | ☑ | ACKNOWLEDGED BY C. JONES AT 12:30 PM TODAY SPOKE TO PATIENT, CONTINUE TO MONITOR, LO... PATIENT'S WEIGHT DOES NOT LOOK... MORE > |
| YESTERDAY 11:35 AM | 186.0 | 142/60 | 88 | 91 | 98.6 | 0/5 | | ACKNOWLEDGED BY C. JONES AT 12:30 PM TODAY SPOKE TO PATIENT, CONTINUE TO MONITOR... PATIENT TOLD ME READINGS OVER THE PHONE. ❤ 180* LBS  PUT ON HOLD BY C. JONES AT 11:00 AM TODAY LEFT PATIENT VOICEMAIL PATIENTS WEIGHT DOES NOT LOOK RIGHT SO MARKED AS INVALID. 123 ~~161.0 LBS~~ ✉ RE-TEST WEIGHT <LESS |
| 01/27/14 10:45 AM | 126.0 📈 | 125/75 | 78 | 96 | 98.6 | 0/5 | ☑ | ACKNOWLEDGED BY C. JONES AT 12:30 PM TODAY SPOKE TO PATIENT, CONTINUE TO MONITOR, LO... PATIENTS WEIGHT DOES NOT LOOK... MORE > |
| 01/05/14 7:00 AM | 112.2 | 137/67 | 67 | 99 | 98.6 | 0/5 | ☑ | ACKNOWLEDGED BY C. JONES AT 12:30 PM TODAY SPOKE TO PATIENT, CONTINUE TO MONITOR, LO... PATIENTS WEIGHT DOES NOT LOOK... MORE > |
| 01/05/14 7:00 AM | 230.0 | 125/75 | 78 | 95 | 98.6 | 0/5 | ☑ | ACKNOWLEDGED BY C. JONES AT 12:30 PM TODAY SPOKE TO PATIENT, CONTINUE TO MONITOR, LO... PATIENTS WEIGHT DOES NOT LOOK... MORE > |
| 12/29/13 3:00 PM | 220.0 - ? | 152/90 - ? | 90 - ? | 80 - ? | 98.6 - ? | 0/5 - ? | ☑ | ACKNOWLEDGED BY C. JONES AT 12:30 PM TODAY |

◂ PAGE [1] OF [1] ▸ BACK TO TOP

| MEMBER NAME | DATE OF LAST TRANSMISSION | QUESTIONS ALERT | WT ALERT | BP ALERT | SPOC ALERT | TEMPERA... ALERT | PAIN ALERT | LAST VIEWED BY |
|---|---|---|---|---|---|---|---|---|
| AARON, ROBIN A. | | | | | | | | LOWE, VALERIE |
| ABBOTT3, PRISCILLA3 | OCTOBER 10, 2012 | | 5.2 LBS | 75mmHg/91mmHg /83 BEATS PER MIN | 98% | 98.2 F | | LOWE, VALERIE |
| ABEL, MATHEW | | | | | | | | LOWE, VALERIE |
| ABISHEK, ARADYA K. | | | | | | | | LOWE, VALERIE |
| ABRAHAM, JENI | | | | | | | | LOWE, VALERIE |
| ALEXANDER3, DOROTHY3 L. | NOVEMBER 7, 2012 | | | 73mmHg/110mmHg /62 BEATS PER MIN | | | | LOWE, VALERIE |
| ALLEN2 HAROLD2 L. | NOVEMBER 30, 2009 | | | | | | | LOWE, VALERIE |
| ALLISON3, CHRISTY3 L. | JANUARY 17, 2011 | | 217.4 LBS | | 96% | | | LOWE, VALERIE |
| ALLISTER, BONNY | OCTOBER 16, 2012 | | 5.0 LBS | 61mmHg/87mmHg /94 BEATS PER MIN | 99% | | | LOWE, VALERIE |
| ALVIN, JAMES | | | | | | | | LOWE, VALERIE |
| ANDREWS, JOPHIN | | | | | | | | LOWE, VALERIE |
| ANSON, SAMUEL | | | | | | | | LOWE, VALERIE |
| ARNOLD, RON R. | JUNE 25, 2010 | | | | | 101 F | 5 | LOWE, VALERIE |
| AUGUSTINE, ROSHAN | | | | | | | | LOWE, VALERIE |
| AXEL, RONY | | | | | | | | LOWE, VALERIE |
| BABY, ROCKY | | | | | | | | LOWE, VALERIE |
| BLADWIN3, EVELYN3 | | | | | | | | LOWE, VALERIE |
| BARTLETT2, JOHNNY2 A. | | | | | | | | LOWE, VALERIE |
| BARTON3, DALE3 | | | | | | | | LOWE, VALERIE |
| BASU, SOBIN | | | | | | | | LOWE, VALERIE |
| BATCHELOR2, SAMANTHA2 | | | | | | | | LOWE, VALERIE |
| BAXTER2, SALLY2 A. | NOVEMBER 17, 2011 | | | | 98% | 98.7 F | 4 | LOWE, VALERIE |
| BEASLEY2, BRUCE2 E. | SEPTEMBER 18, 2009 | | 300.5 LBS | | 100% | 100.6 F | 1 | LOWE, VALERIE |
| BEN, ASHISH | | | | | | | | LOWE, VALERIE |
| BENJAMIN, JACK | NOVEMBER 15, 2012 | | 275 LBS | | 98% | | | LOWE, VALERIE |
| BERNARLD, LEO | | | | | | | | LOWE, VALERIE |

| MEMBER NAME | FAHED, ISSAC ▼ | | | | RUN REPORT |
|---|---|---|---|---|---|
| START DATE | 01/24/2013 | CALENDER MM/DD/YYYY | END DATE | 02/26/2013 | CALENDER MM/DD/YYYY |

MEMBER INFROMATION

| NAME: FAHED, ISSAC | PHONE: 56756757 |
|---|---|
| SSN: 567334434 | ID: |

WEIGHT [GRAPH]

| | MOST RECENT LIMITS | | | |
|---|---|---|---|---|
| HIGH RISK | MODERATE RISK | NORMAL RANGE | MODERATE RISK | HIGH RISK |
| BELOW 0 | NONE | 0 - 0 | NONE | ABOVE 0 |

| MEASUREMENT | TRANSMIT DATE | ▼ MEASUREMENT DATE | LBS |
|---|---|---|---:|
| WT | 2/22/2013 4:59:40 PM | 2/22/2013 4:59:34 PM | 66.8 |
| WT | 2/21/2013 11:56:17 PM | 2/21/2013 11:55:55 PM | 88.8 |
| WT | 2/19/2013 4:39:07 PM | 2/19/2013 4:38:49 PM | 38.8 |
| WT | 2/19/2013 4:35:20 PM | 2/19/2013 4:35:02 PM | 86.8 |
| WT | 2/19/2013 4:32:44 PM | 2/19/2013 4:32:25 PM | 98.8 |
| WT | 2/19/2013 4:31:46 PM | 2/19/2013 4:31:26 PM | 97.8 |
| WT | 2/19/2013 10:50:06 PM | 2/19/2013 10:49:47 PM | 88.8 |
| WT | 2/19/2013 10:45:51 PM | 2/19/2013 10:45:30 PM | 57.9 |
| WT | 2/1/2013 6:07:47 PM | 2/19/2013 6:07:36 PM | 0.9 |
| WT | 2/1/2013 6:05:32 PM | 2/19/2013 6:05:21 PM | 2.9 |
| WT | 2/1/2013 5:54:30 PM | 2/19/2013 5:54:18 PM | 2.9 |
| WT | 2/1/2013 5:51:31 PM | 2/19/2013 5:51:21 PM | 4.9 |
| WT | 2/1/2013 5:42:25 PM | 2/19/2013 5:42:13 PM | 2.0 |
| WT | 2/1/2013 5:14:46 PM | 2/19/2013 5:14:13 PM | 2.0 |
| WT | 2/1/2013 5:12:48 PM | 2/19/2013 5:12:38 PM | 4.9 |
| WT | 2/1/2013 5:11:57 PM | 2/19/2013 5:11:44 PM | 4.9 |
| WT | 2/1/2013 2:36:27 PM | 2/19/2013 2:36:02 PM | 4.9 |
| WT | 2/1/2013 2:04:23 PM | 2/19/2013 2:04:07 PM | 4.9 |
| WT | 2/1/2013 11:53:16 AM | 2/19/2013 11:53:02 AM | 77.8 |
| WT | 2/1/2013 11:50:36 AM | 2/19/2013 11:50:24 AM | 44.9 |
| WT | 2/1/2013 11:45:12 AM | 2/19/2013 11:44:39 AM | 44.9 |
| WT | 2/1/2013 11:41:03 AM | 2/19/2013 11:40:47 AM | 44.9 |

QUESTIONS

| TRANSMIT DATE | ▼ MEASUREMENT DATE | QUESTION | ANSWER |
|---|---|---|---|
| 2/19/2013 4:35:30 PM | 2/19/2013 4:35:15 PM | ARE YOUR CLOTHES TIGHTER AT THE WAIST THAN USUAL? | NO |

| EQUIPMENT | 100299 [TABLET] | | |
|---|---|---|---|
| EQUIPMENT INFORMATION | | | |
| *EQUIPMENT TYPE | TABLET | | |
| *LAST 6 DIGITE OF SERIAL NUMBER | 100299 | | |
| *EQUIPMENT TIME | SERVER TIME | | |
| MEMBER(S) ASSIGNED TO THE EQUIPMENT | | | |
| JAMES JONATHAN | | | |
| | | SAVE | SAVE |

| MEMBER NAME | JAMES, JONATHAN | | | | SAVE |
|---|---|---|---|---|---|
| — ASSIGNED EQUIPMENTS | | | | | |
| NONE | | | | | |
| ADD/UPDATE EQUIPMENT | ANDROID TABLET | | | | |
| — VITAL SIGNS | | | | | |
| ☐ BLOOD GLUCOSE | ROCHE/ACCU-CHECK AVIVA | | | | |
| ☐ BLOOD OXYGEN | NONIN/9660-BLUETOOTH | *ID | 001C03012562 | *SN | 790960 |
| ☐ BLOOD PRESSURE | A&D UA-767PBT | | | | |
| ☐ PAIN | PAIN RATING (0 - 10 SCALE) | | | | |
| ☐ TEMPATURE | MANUAL ENTRY TYPE | ⦿ F  ○ C | | | |
| ☒ WEIGHT | A&D UC-321PBT | ⦿ LBS  ○ KG | | | |
| — QUESTIONS | | | | | |
| ☒ QUESTIONS SET 5 | ☒ QUESTIONS SET 4 | | ☐ QUESTIONS SET 3 | | |
| ☐ QUESTIONS SET 2 | ☐ QUESTIONS SET 1 | | | | |
| — EQUIPMENTS | | | | | |
| SELECT EQUIPMENT | 100299 | | | | |
| EQUIPMENT LOGIN INFORMATION | | | | | |
| *SCREEN NAME | JAMES | PASSCODE | 1 | | |
| | | SAVE | | | |

Fig. 25

COMPUTER READABLE STORAGE MEDIA FOR REMOTE PATIENT MANAGEMENT AND METHODS AND SYSTEMS FOR UTILIZING SAME

TECHNICAL FIELD

Embodiments of the present disclosure relate generally to healthcare, and more specifically to remote patient management.

BACKGROUND

Remote patient management systems are often used to allow for the provision of healthcare to patients remotely located from medical facilities and medical practitioners. For example, such systems may allow patients to receive healthcare in their respective residences. When receiving healthcare in this manner, patients often interact with one or more medical practitioners, using various devices to communicate and exchange medical data. In many cases, however, patients may rely on devices that compromise the effectiveness of healthcare received. For example, devices used by patients may become outdated and/or may provide inaccurate measurements of patient vitals. In either case, replacing and/or recalling the device may present challenges in existing remote patient management systems.

SUMMARY

Systems and methods for remote patient management, according to certain implementations, involve receiving an enrollment request to enroll a patient, identification of vitals of the patient to be measured based on the enrollment request, providing an equipment request indicating the vitals of the patient to be measured, receiving equipment information corresponding to one or more health measurement devices for measuring the vitals of the patient, and associating the patient with the equipment information corresponding to the one or more health measurement devices.

According to additional or alternative implementations, a computer implemented system or method involves establishing, using a user device, communication with a health measurement device, wherein the user device is associated with a patient. The user device determines whether the health measurement device is associated with the patient. If so, one or more measurements are received from the health measurement device, and the one or more measurements are provided to a healthcare management server. If not, no measurements from the health measurement device are received.

According to additional or alternative implementations, a method involves receiving an equipment request and identifying health measurement devices based on the equipment request. For each of the health measurement devices, equipment information associated with the health measurement device is provided, and this information may include a serial number, a model number, an identification number, a version number, or a combination thereof.

BRIEF DESCRIPTION OF THE DRAWINGS

FIGS. 5-21 are various screenshots of a graphical user interface (GUI) for facilitating remote patient according to an embodiment of the present disclosure.

FIGS. 22-25 are various screenshots of a GUI for facilitating remote patient management according to an embodiment of the present disclosure.

DETAILED DESCRIPTION

Systems and methods for remote patient management are disclosed herein. Certain details are set forth below to provide a sufficient understanding of embodiments of the disclosure. However, embodiments of the disclosure may be practiced without these particular details. Moreover, the particular embodiments are provided by way of example and should not be construed as limiting. In other instances, well-known circuits, control signals, timing protocols, and software operations have not been shown in detail to avoid unnecessarily obscuring the invention.

Figure 1:
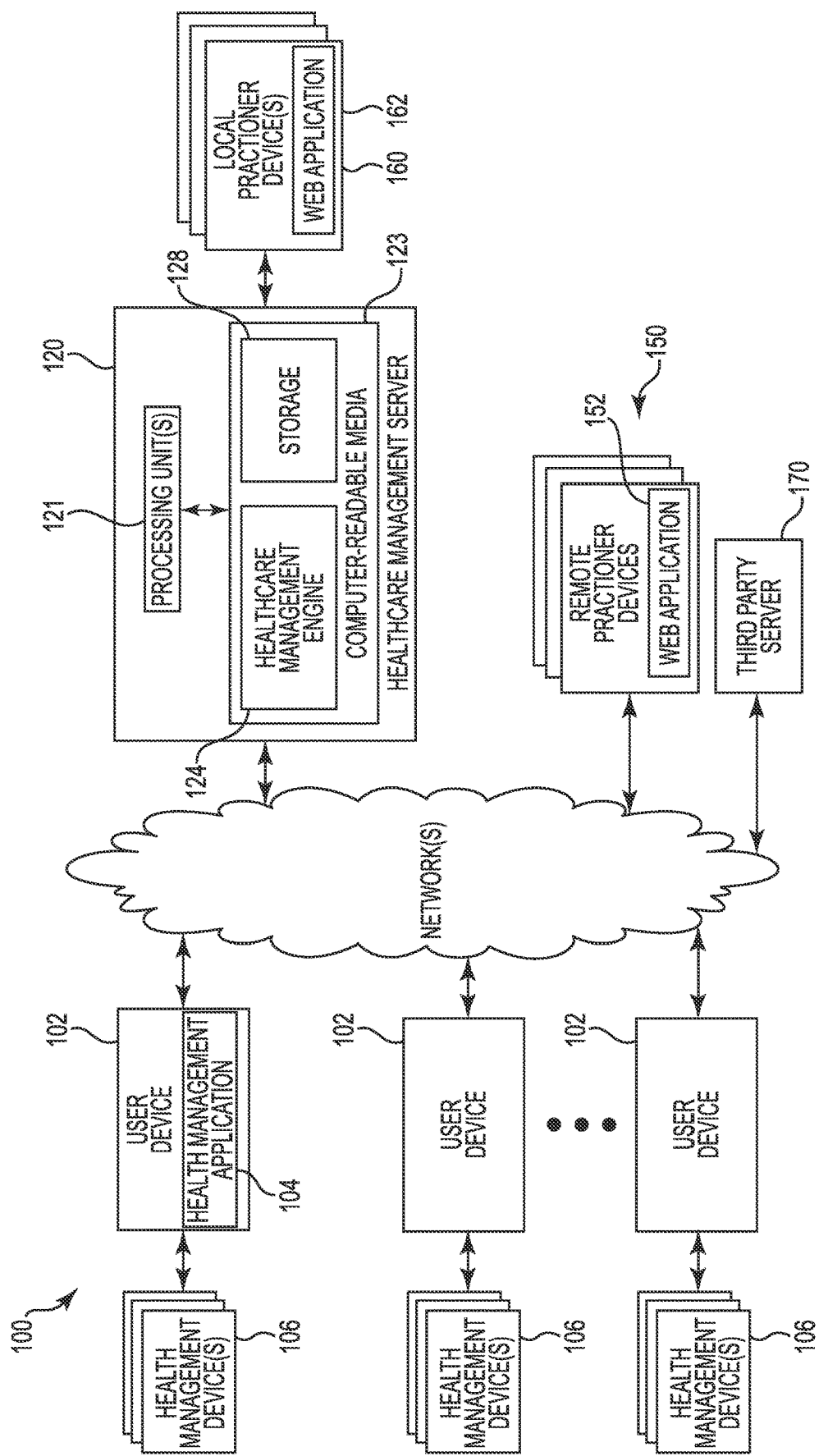
FIG. 1 is a schematic diagram of a computer networking environment according to an embodiment of the present disclosure.

FIG. 1 is a schematic diagram of a computer networking environment 100 according to an embodiment of the invention. Each of a plurality of user devices 102 may be remotely located from other components of the computer networking environment 100, and once provided to a patient, may be located at a patient's home or primary place of residence. The user devices 102 may comprise a computing device, including but not limited to a tablet, router, gateway, server, thin client, laptop, desktop, media device, smartphone, television, phablet, cellular device or other mobile device, modem, or any combination or sub-combination of the same. Each of the plurality of user devices 102 may include a memory encoded with one or more modules of executable instructions that may operate in conjunction with one or more processing units of the user device 102 to provide functionality allowing execution of a health measurement application 104. In some implementations, the user devices 102 may be limited for use as remote patient management devices.

Each of the user devices 102 may be configured to communicate with one or more health measurement devices 106, for instance, using a respective health measurement application 104. Each of the health measurement devices 106 may be configured to measure one or more vitals of a user and/or provide the measurement(s) to the health measurement application 104. By way of example, the health measurement devices 106 may include but are not limited to scales, glucose monitors, oxygen monitors, blood pressure monitors, thermometers, heart rate monitors, and any combination or sub-combination of the same. In some examples, health measurement devices 106 may be configured to measure vitals of a patient and provide the measurements to a health measurement application 104 electronically (e.g., using a wired or wireless network). Additionally or alternatively, a patient may use one or more health measurement devices 106 to measure vitals and subsequently input the measurements in the health measurement application 104 manually.

Each of the user devices 102 may be further configured to communicate over a network 110 with any number of devices, including but not limited to the healthcare management server 120. The network 110 may comprise one or more networks, such as local area networks (LANs), wide area networks (WANs), metropolitan area networks (MANs), cellular networks, and/or the Internet. Communications provided to, from, and within the network 110 may be wired and/or wireless, and further may be provided by any networking devices known in the art, now or in the future. Devices communicating over the network 110 may communicate with any communication protocol, including TCP/IP and UDP protocols, as well as HTTP, HTTPS, SSL, or any protocol derived therefrom.

The healthcare management server 120 may include one or more processing units 121 and computer readable media 123. Herein, the term computer readable media is used to refer to a single computer readable medium in some embodiments, and in other embodiments multiple computer readable media in communication with one or more processing units, such as the processing units 121. The computer readable media 123 may also include a storage 128. The executable instructions for a healthcare management engine 124 may include instructions for managing healthcare of one or more users (e.g., patients) of user devices 102, further examples of which are provided below. Although the executable instructions for the healthcare management engine 124 are shown on a same computer readable media 123, in some embodiments, any or all sets of instructions may be provided on multiple computer readable media and may not be resident on the same media. Accordingly, computer readable media 123 as used herein includes one or more computer readable media 123 and/or the storage 128. Computer readable media 123 and/or storage 128 may include any form of computer readable storage or computer readable memory, transitory or non-transitory, including but not limited to, externally or internally attached hard disk drives, solid-state storage (such as NAND flash or NOR flash media), tiered storage solutions, storage area networks, network attached storage, and/or optical storage. As described, the instructions stored on the computer readable media 123 may be executed on the one or more processing units 121 or other processing units. The executable instructions for the healthcare management engine 124 may be referred to as a "healthcare management engine" herein, where the healthcare management engine refers to the executable instructions for a healthcare management engine 124 executed by the one or more of the processing units 121 and/or other processing units.

The storage 128 may include information (e.g., data) that may be utilized by one or more of the processing units 121 during execution of the healthcare management engine 124. By way of example, the storage 128 may include healthcare information including but not limited to patient information (e.g., vitals measurements, medical history, contact information), ranges (e.g., ranges for blood pressure), clinician data (e.g., notes associated patient visits), and insurance information (e.g., providers, plans).

In some examples, healthcare information stored on the healthcare management server 120 may be accessed by a practitioner using a remote practitioner device 150 and/or a local practitioner device 160. For example, each remote practitioner device 150 may include a web application 152 and each local practitioner device 160 may include a web application 162. Each web application 152, 162 may be an application, such as a browser, that operates in accordance with one or more web-based programming languages and may be configured to access one or more services, such as a GUI, provided by the healthcare management server 120. Practitioners, such as nurses or doctors, may use respective applications 152, 162 to access healthcare information located on the healthcare management server 120 and further may perform healthcare management in accordance with examples described herein. In some examples, web applications 152 executing on remote practitioner devices 150 may access healthcare information using a first interface (e.g., GUI), and web applications 162 executing on local practitioner devices 160 may access healthcare information using a second interface. By way of example, web applications 152 may operate according to a GUI illustrated in FIGS. 5-21 and web applications 162 may operate according to a GUI illustrated in FIGS. 22-25. In another example, web applications 162 may operate according to the GUI illustrated in FIGS. 5-21 and web applications 152 may operate according to the GUI illustrated in FIGS. 22-25. Each practitioner device 150, 160 may comprise any computing device, including but not limited to a tablet, router, gateway, server, thin client, laptop, desktop, media device, smartphone, television, phablet, cellular device or other mobile device, modem, or any combination or sub-combination of the same. In some examples, remote practitioner devices 150 may be externally located relative to the healthcare management server 120 (e.g., located on an external network) and local practitioner devices 160 may be internally located relative to the healthcare management server 120 (e.g., located on a same network). Accordingly, remote practitioner devices 150 may be configured to communicate with the healthcare management server 120 using the network 110 and the local practitioner devices 160 may be configured to communicate with the healthcare management server 120 using a private network (not shown in FIG. 2) and/or the network 110. While examples described herein are directed to web applications 152 using a first interface and web applications 162 using a second interface, it will be appreciated that each web application 152, 162 may use any interface known now or in the future.

In some examples, the healthcare management server 120 may further be configured to communicate with a third party server 170. The third party server 170 may, for instance, be associated with a vendor, such as a hardware vendor. As described further herein, the healthcare management server 170 may provide equipment requests to the third party server 170 identifying one or more vitals of a patient and/or health measurement devices 106 for measuring the one or more vitals. In response to receipt of an equipment request, the third party server 170 may cause a user device 102 and/or one or more health measurement devices 106 to be assigned and/or made available to a patient.

Generally, the computer networking environment 100 may serve to provide remote patient management. A practitioner may employ a remote practitioner device 150 or a local practitioner device 160 to interface with the healthcare management engine and request a patient be enrolled in remote patient management. Based on the enrollment request, the healthcare management engine may cause one or more health measurement devices 106 to be provided to the patient for measuring one or more vitals (e.g., blood pressure, weight) of the patient. The healthcare management engine further may associate the provided health measurement devices 106 with the patient, for instance, based on unique serial numbers and/or identification numbers of the health measurement devices 106 provided to the patient. In this manner, the healthcare management engine may control operability of health measurement devices 106 by the user to ensure that the patient uses only those health measurement devices 106 provided in accordance with the enrollment process. In some examples, a user device 102 may be provided to a patient in addition to health measurement devices 106 and the user device 102 may be associated with the patient in the same or similar manner to associating the health measurement devices 106. Moreover, the user device 102 may be associated with only those health measurement devices 106 associated with the patient (e.g., by unique serial number or other unique identification number) to ensure the user device 102 does not receive signals or information from other health measurement devices not assigned to the patient, such as measurement devices with wireless capabilities that are within a close proximity to the user device 102, or wired measurement devices that can be communicatively coupled with the user device 102 that may otherwise be sensed by the user device 102. The user device 102 may be configured to operate with one or more health measurement devices 106 prior to the user device 102 being provided to the patient, or may be configured to operate with the one or more health measurement devices 106 by the patient. By providing health measurement devices 106 and/or user device 102 to a patient and further associating the patient with the health measurement devices 106 and/or user device 102, examples of remote patient management described herein may ensure that a patient receives healthcare using information from the health measurement devices 106 and/or user device 102 that are accurate, up-to-date, and compatible with the healthcare management engine. The devices provided to the patient for engagement in remote patient management differ from other healthcare management devices that are facility-based (e.g., within a hospital or at a provider location) because such devices configured to remain within a facility and are not assigned to a patient, and instead are configured to measure vital signs of multiple patients. In contrast, the device(s) provided to the patient in the remote patient management are portable and specifically assigned to the patient, such that if the patient moves his or her principal place of residence, the device(s) may follow the patient. In addition, as described, measurement devices 106 transmit vital signs to the healthcare management engine via the user device 102 after at least the measurement devices 106 have been assigned to the patient.

Providing and/or configuring devices in this manner may result in improved patient convenience. By way of example, providing vitals measurements using remote patient management may reduce the number of hospital visits (e.g., for check-ups) required for each patient. For instance, regularly monitoring the patient's health using health measurement devices communicatively coupled to the user device operated by the patient at his/her place of residence may allow the patient to be monitored by a healthcare professional engaged in the networking environment 100 so the patient's condition can be addressed using interventions offered by the healthcare professional but controlled by the patient or a home care nurse rather than by personnel at hospitals or other healthcare facilities. Due to the added convenience, patient participation may also be improved as patients unable or unwilling to attend hospital check-ups may still be able or willing to provide measurements from their own respective homes. Providing and/or configuring devices in this manner may further result in more reliable remote patient management. By way of example, assigning devices (a user device and/or one or more health measurement devices) to a specific patient may ensure that only properly operating and compatible devices are used to measure respective vitals. Moreover, in some examples, devices may require authentication of the patient to ensure that the devices are used only by the patient assigned to the devices. Furthermore, user devices may be re-configured to operate with replacement devices when, for instance, an original health monitoring device assigned to the user device breaks. In this example, the user device may receive a re-configuration update from an administrative module associated with the networking environment in which the replacement device is assigned to the user device, while disabling receipt of signals from the original health monitoring device.

Once enrolled in remote patient management and in possession of assigned health measurement devices 106, a patient may act in accordance with remote patient management. For example, a patient may use the health measurement devices 106 to measure one or more vitals identified by a practitioner during or after the enrollment process. Measurements and other feedback (e.g., answers to questions) may be provided from the health measurement devices 106 to the user device 102 (e.g., electronically or manually) and in turn from the user device 102 to the healthcare management engine. In some examples, the user device 102 and/or the health measurement devices 106 may be "pre-registered" for a patient. That is, the user device 102 and/or the health measurement devices 106 may be configured for use by the patient without requiring any additional configuration by or authentication of the patient.

Thereafter, a practitioner may access the healthcare management engine to monitor and/or manage healthcare of the patient. By way of example, a practitioner may analyze measurements, communicate with the patient (e.g., using voice, text and/or video), maintain clinician notes, and set parameters for usage of the health measurement devices 106 by one or more patients. Analyzing measurements may include determining whether a patient's vitals exceed a particular range and/or whether a patient's vitals have a relatively high amount of variance over a particular amount of time. Communicating with the patient may include exchanging messages with the patient and/or providing questions to and receiving answers from the patient. In some examples, messages, questions, answers, and other communications may be exchanged with the patient using the health management application 104 of the user device 102. The health measurement application 104 may, for instance, present the patient with one or more questions each time a patient provides measurements. Setting parameters for patient usage of the health measurement devices 106 may include defining a schedule for a patient's measurements, defining alerts for the patient and/or practitioner when a patient deviates from the schedule and/or measurements exceed a particular range, and assigning one or more health measurement devices 106 to a patient.

Figure 2:
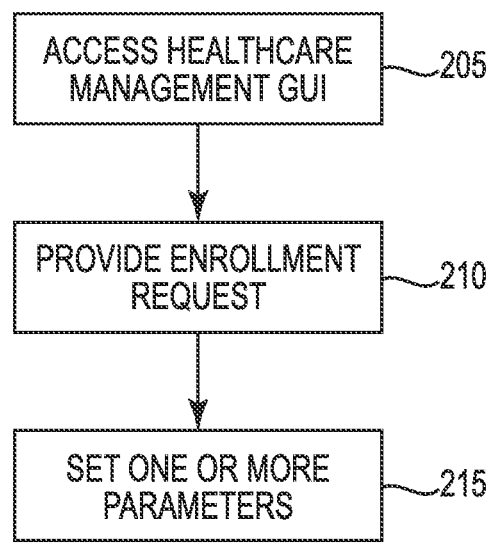
FIG. 2 is a flowchart of a method for requesting enrollment of a patient in remote patient management according to an embodiment of the present disclosure.

FIG. 2 is a flowchart of a method 200 for requesting enrollment of a patient in remote patient management according to an embodiment of the present disclosure. The method 300 may be implemented using either a web application 152 of a remote practitioner device 150 or a web application 162 of a local practitioner device 160 of FIG. 1. Accordingly, while examples are described herein with reference to a web application 152, it will be appreciated that described examples may be applicable to use of a web application 162 or any other web application as well.

At a step 205, a practitioner may access a healthcare management engine GUI using the web application 152 of a remote practitioner device 150. This may, for instance, include authenticating with a portal provided by the healthcare management engine. Once authenticated, at a step 210, the practitioner may request a patient be enrolled in remote healthcare management. Requests provided in this manner may include providing patient information, such as contact information, insurance information, emergency contact information, and patient medical history, that may be used to provide an account and/or medical record for the patient. In some examples, enrollment requests may include information as to the nature in which remote patient management is to be administered to the patient. For example, the practitioner may identify vitals of the patient to be measured, the manner in which the vitals are to be measured (schedule, etc.), the health measurement devices 106 that are to be used to measure the vitals of the patient, and/or a type of remote monitoring program the patient is to be enrolled such as a congestive heart failure (CHF) program; a chronic obstructive pulmonary disease (COPD) program and/or a diabetes program.

While the step 205 is described with respect to a request being provided, for instance, to the healthcare management engine, it will be appreciated that the step 205 may be performed using several discrete acts. For instance, in some examples the practitioner may request that an account is created for a patient, and once the account is created, other aspects of the patient's healthcare may be established. In some examples, the account may be created by a health insurance provider administering insurance to the patient that may additionally administer care to the patient using practitioners employed by or contracted by the health insurance provider. Vitals to be measured and devices for measuring the vitals, for instance, may all be specified for a patient after an account for the patient has been provided.

Once patient enrollment has been completed, one or more health measurement devices 106 may be provided to the patient, and the patient may use the health measurement devices 106 to measure one or more respective vitals. Accordingly, after providing the request at the step 210, the practitioner may set one or more parameters for operation of the health measurement devices 106 associated with the patient at a step 215. The step 215 may be performed either prior to a patient receiving the health measurement devices 106 or may be performed after a patient receives the health measurement devices 106. In at least one example, setting parameters in this manner may include defining a preferred range of vitals measurements. A practitioner may, for instance, set a systolic blood pressure range of 100-160 mmHg, and should a patient's measurements exceed this range, the practitioner may be notified and/or the patient may be encouraged to seek medical attention. In another example, setting parameters may include setting a schedule for measurement of one or more vitals. Parameters may be set based on industry practices or guidelines or may be based on those adopted by a practitioner group. In some instances, the health measurement devices 106 and/or user device 102 may inform a practitioner and/or patient when a patient has failed to measure vitals in accordance with the schedule or is at risk of failing to measure vitals in accordance with the schedule.

Figure 3:
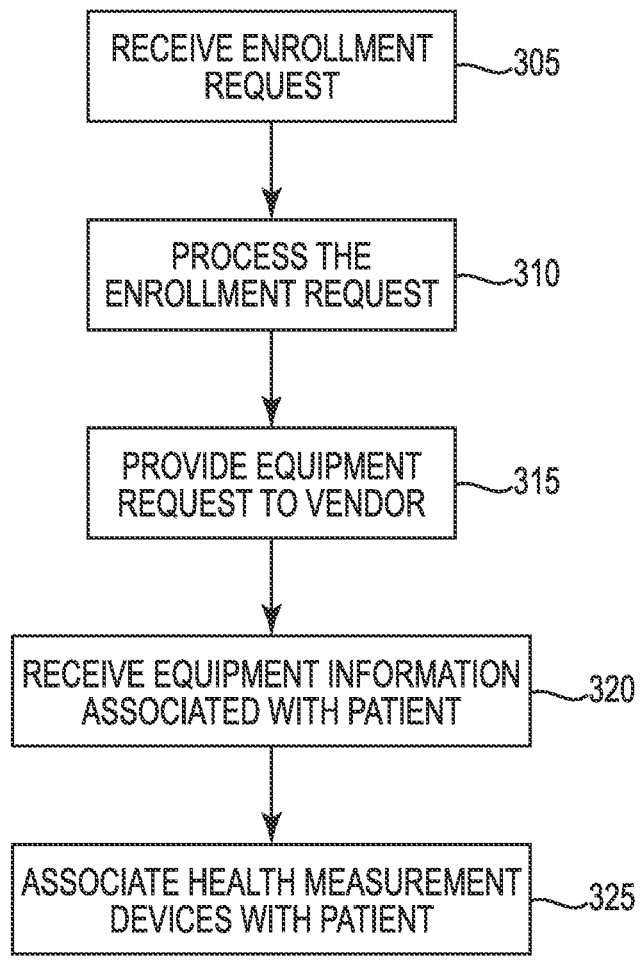
FIG. 3 is a flowchart of a method for enrolling a patient in remote patient management according to an embodiment of the present disclosure.

FIG. 3 is a flowchart of a method 300 for enrolling a patient in remote patient management according to an embodiment of the present disclosure. The method 300 may be implemented using the healthcare management server 120 of FIG. 1, and in particular, may be implemented using the healthcare management engine of the enterprise server 120.

At a step 305, the healthcare management engine may receive an enrollment request. As described with respect to the step 210 of FIG. 2, the enrollment request may be provided by a remote practitioner device 150 or a local practitioner device 160, and further may be provided using a GUI of the healthcare management engine. In response to receipt of the enrollment request, the healthcare management engine may process the enrollment request at a step 310. The healthcare management engine may, for instance, add a patient to a list of enrolled patients and/or may provide (e.g., generate) an account for the patient. The account may include information identified by the enrollment request including but not limited to patient information, vitals of the patient to be measured, the manner in which the vitals are to be measured (schedule, etc.), the health measurement devices 106 that are to be used to measure the vitals of the patient, and/or a type of remote monitoring program the patient is to be enrolled such as a congestive heart failure (CHF) program; a chronic obstructive pulmonary disease (COPD) program and/or a diabetes program. While enrollment requests received by the healthcare management engine have been described as identifying health measurement devices 106 to be used to measure the vitals of the patient, in some instances, enrollment requests may only identify vitals of the patient to be measured or the program(s) in which the patient is to be enrolled. Accordingly, in some examples the healthcare management engine may determine which health measurement devices are to be used to measure vitals of the patient based on the enrollment request.

Figure 4:
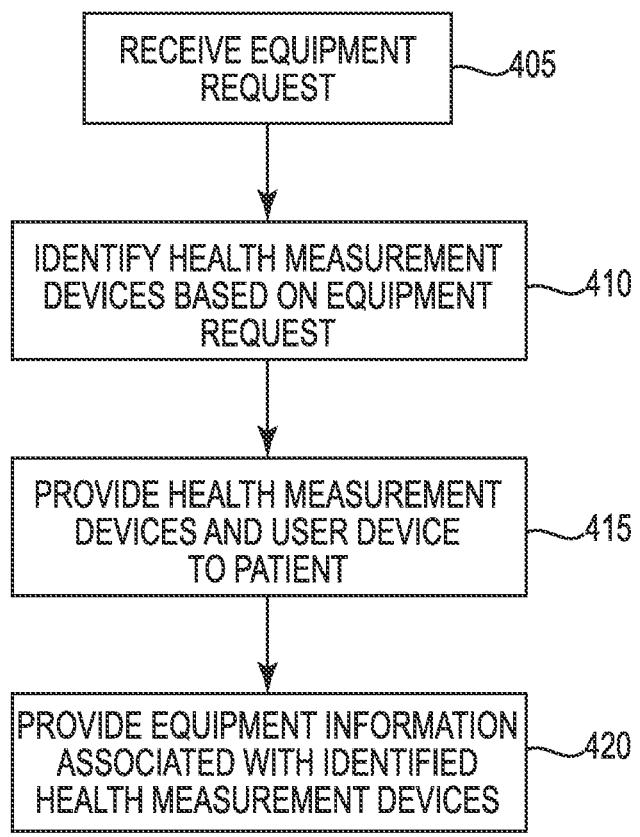
FIG. 4 is a flowchart of a method for associating equipment with a patient enrolled in remote patient management according to an embodiment of the present disclosure.

Once the enrollment request has been processed, the healthcare management system may provide an equipment request to the third party server 170 at a step 315. The equipment request may identify vitals to be measured and/or health measurement devices 106 for measuring the same. With reference to the method 400 of FIG. 4, the third party server 170 may receive the equipment request at a step 405 and in response, may identify one or more health measurement devices 106 based on the equipment request at a step 410. If the equipment request identifies health measurement devices 106, the third party server 170 may identify the health measurement devices 106 enumerated in the request. If the equipment request does not identify health measurement devices 106, the third party server 170 may determine which health measurement devices 106 correspond to the vitals identified by the equipment request.

Once health measurement devices 106 have been identified at the step 410, the third party server 170 may provide the identified health measurement devices 106 and/or a user device 102 to the patient at a step 415. For instance, the third party server 170 may cause the identified health measurement devices 106 to be shipped to or otherwise made available to the patient. At a step 420, the third party server 170 may further provide equipment information associated with the identified health measurement devices 106 to the healthcare management engine. Equipment information provided in this manner may include unique serial numbers, model numbers, version numbers, and/or identification numbers uniquely identifying each of the identified health measurement devices 106.

In some examples, a user associated with the third party server 170 may configure the user device 102 and/or health measurement devices 106. The user may associate the user device 102 and the health measurement devices 106 with a patient, for instance, based on the equipment request. The user may enter patient information into the user device 102 and/or the health measurement devices 106 to associate the user device 102 and/or the health measurement devices 106 with a patient. The user may further associate the user device 102 and the health measurement devices 106 with each another. This may include configuring the user device 102 to operate only with one or more particular health measurement devices 106 and/or with the health management engine. For example, the user device 102 may be configured to include and/or execute only the web application 104 and/or any other services required for remote patient management. In other examples, the user device 102 and/or one or more health measurement devices 106 may be pre-configured, for instance by a manufacturer, prior to being provided to the user associated with the third party server 170. As a result, the user associated with the third party server 170 need not configure the user device 102 or health measurement devices 106 when providing the same to a patient.

Referring back to FIG. 3, after providing an equipment request to the third party server 170 at the step 315, the healthcare management engine may receive equipment information at a step 320. The healthcare management engine may associate the patient with each of the healthcare measurement devices 106 associated with the received equipment information at a step 325.

By associating the received equipment information with a patient, the healthcare management engine may control operability of health measurement devices 106. As described, a patient may receive a health measurement device 106 during an enrollment process, and the healthcare management engine may receive equipment information corresponding to the health measurement device 106. Subsequently, the healthcare management engine may associate the equipment information with the patient and/or provide the equipment information to the user device 102. Following a measurement with the health measurement device 106, the health measurement device 106 may provide the measurement to a user device 102 of the patient. In turn, the user device 102 may provide the measurement to the healthcare management engine. If, however, the patient uses a health measurement device that was not received during the enrollment process, the measurement may be rejected by either the health management application 104 of the user device 102 or the healthcare management engine. By way of example, the health management application may receive equipment information for each of the health measurement devices 106 provided to a patient during enrollment. If a measurement is received from a health measurement device not matching an associated health measurement device 106, the health management application 104 may reject the measurement and/or all communication with the health measurement device. In another example, the healthcare management engine may determine whether measurements are provided by health measurement devices 106 provided during enrollment.

While the methods 200, 300, and 400 have been described as including particular steps, it will be appreciated that in some instances additional steps may be included the methods 200, 300, and 400, and/or one or more described steps of the methods 200, 300, and 400 may be modified or omitted. By way of example, with reference to FIG. 4, in some examples, the step 420 may be performed before the step 415. That is, the third party server 170 may provide equipment information prior to causing health measurement devices 106 to be provided to a patient. In another example, the healthcare management engine may cause health measurement devices 106 to be provided to a patient without providing an equipment request to the third party server 170.

FIGS. 5-21 are various screenshots of a GUI for facilitating remote patient management according to an embodiment of the present disclosure. The GUI described herein with reference to FIGS. 5-21 may be used to implement a GUI utilized by remote practitioner devices 150. It will be appreciated by those having skill in the art that any and all patient information (e.g., data) provided in FIGS. 5-21 is provided for the purposes of illustration only and in no way comprises actual patient information.

FIG. 5 is a screenshot 500 of a GUI (e.g., dashboard) that may be used to manage one or more patients enrolled in remote patient management. The GUI may be displayed in response to a practitioner being authenticated with the healthcare management engine. As illustrated in the screenshot 500, a list of patients and various vitals for each patient may be viewed simultaneously. In particular, a practitioner name 1002 may be presented, for instance, to indicate which practitioner is currently authenticated and using of the GUI. In some examples, those patients listed in the GUI may be only those patients associated with the practitioner. Although a single measurement is shown for each type of vital, an expansion box 1004 may be selected to expand (or collapse) a patient's measurements. Measurements added since the practitioner last viewed the GUI may be highlighted in some examples.

The GUI may further feature several icons to facilitate use of the GUI. In at least one example, measurements exceeding a specified range may be flagged, for instance, using a flag 1006, and the color, size, or shape of the flag may be used to indicate the degree to which the measurement exceeds the range. In another example, a graph icon 1008 may be used to indicate a high variance between patient measurements. By way of example, if a patient loses or gains a relatively high amount of weight over a relatively short amount of time, the graph icon 1008 may be used to note the variance. A lock icon 1009 may be used to indicate that a patient is suspended. This may, for instance, be used to indicate that a patient is unable to provide measurements, and any alerts that would otherwise arise from a patient failing to provide measurements may be suppressed. A first clipboard icon 1010 having a lock and a second clipboard icon 1011 having no lock may be used to indicate that a patient's measurements are not on hold and on hold, respectively. Placing a patient's measurements on hold may indicate that a patient has been requested to re-measure one or more vitals and that the measurements will remain on hold until the patient fulfills the request.

In some examples, a practitioner may review additional details about a patient by selecting an information icon 1012 on the GUI. As illustrated in the screenshot 600, clinician notes 1014, medical history 1015, and patient information 1016 (e.g., contact information, emergency contact information, care provider information), may all simultaneously be displayed for a patient in response to selecting the information icon 1012.

In some examples, hovering over a particular measurement may display one or more parameters associated with a measurement. Hovering over a measurement may display a recommended range and/or measurement interval for the measurement. As illustrated in the screenshot 700, hovering over a measurement 1018 may display a parameter window 1020 including recommended ranges for systolic and diastolic blood pressure, respectively.

In some examples, hovering over a questions and answers (Q&A) field may display one or more questions provided to and/or answered by a patient. With reference to FIG. 8, for instance, hovering over a Q&A field 1022 may display a Q&A window 1024 including a plurality of questions answered by a patient. These answers may be utilized by a practitioner to provide remote patient management to the patient. The GUI may indicate a number of answers provided by the patient that may require further analysis or inquiry, for instance, due to the patient providing a cautionary answer.

Figure 9:
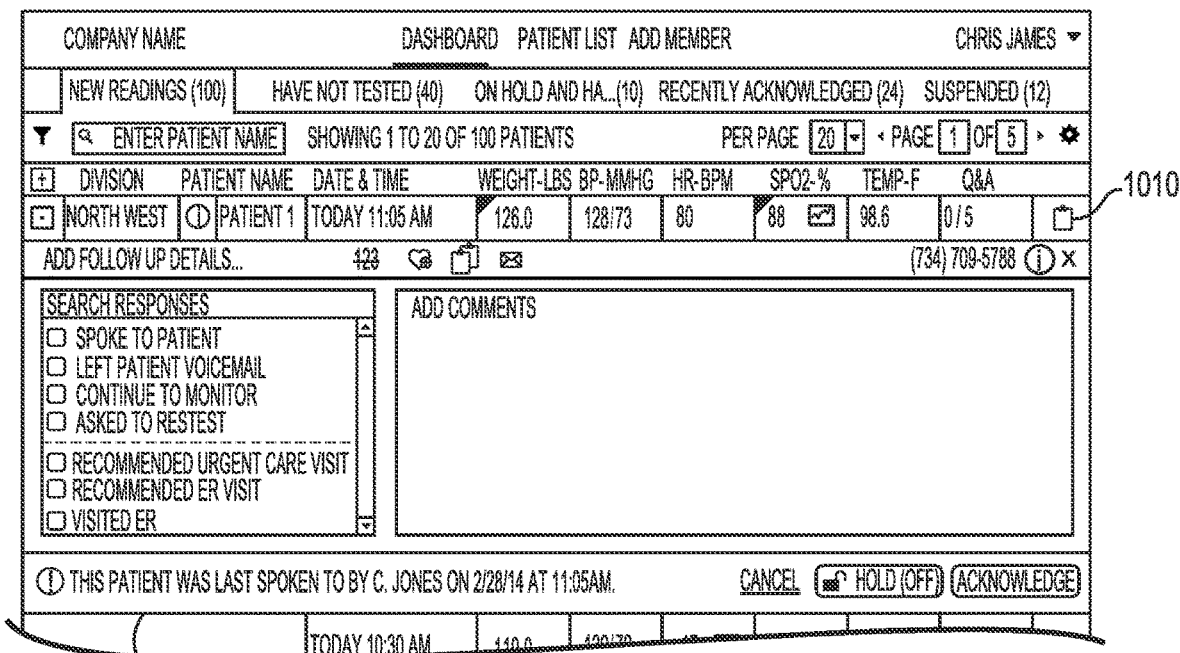
Figure 16:
Figure 17:
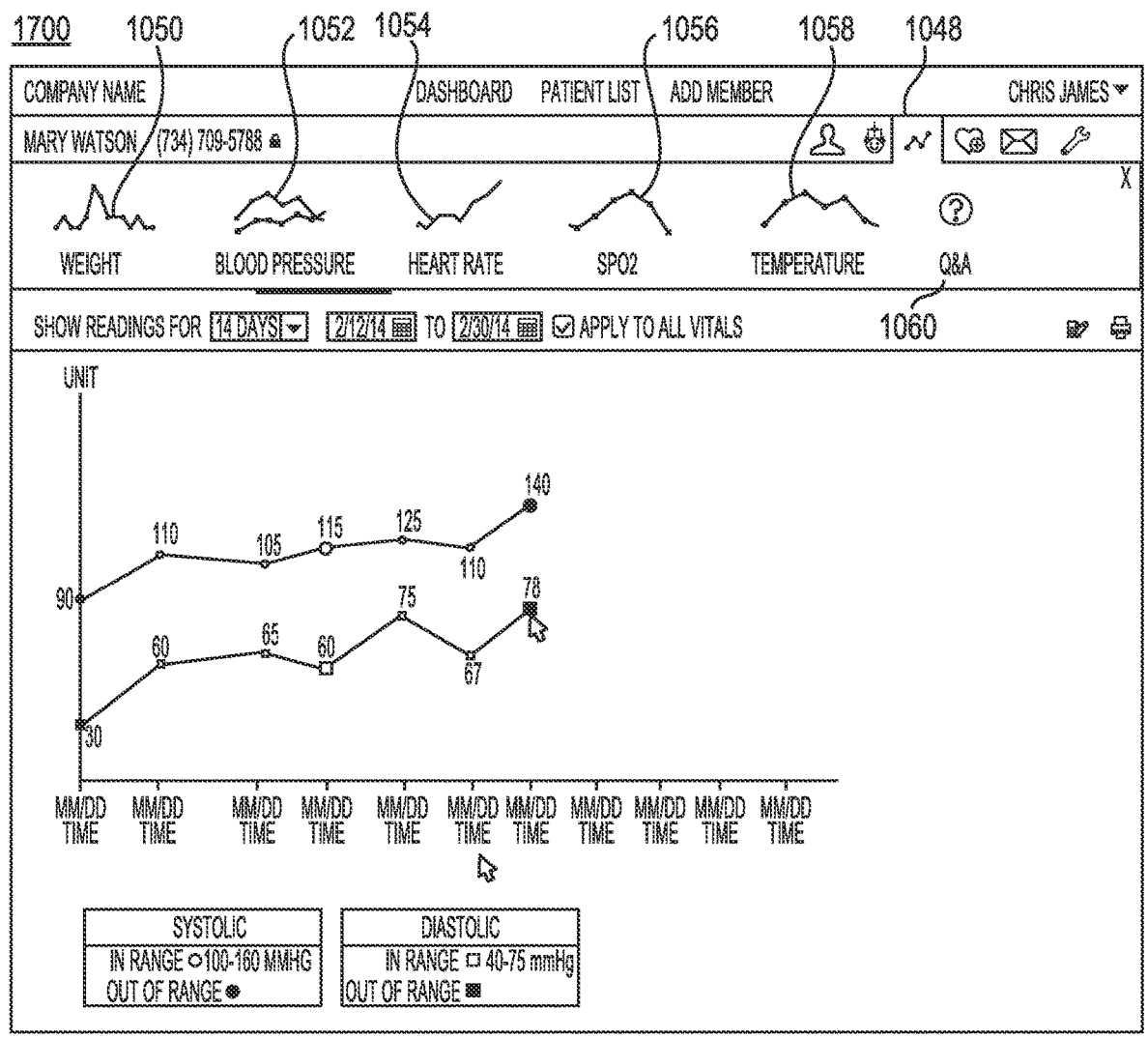
Figure 19:
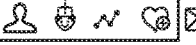

FIG. 9 is a screenshot 900 illustrating features directed to a response window 1030. The response window 1030 may displayed in response to selection of a response icon 1010 and may be used to acknowledge and analyze one or measurements. By way of example, the response window 1030 may be used to invalidate measurements, request new measurements, adjust measurements, provide comments regarding measurements, message a patient, and adjust measurements.

Figure 10:
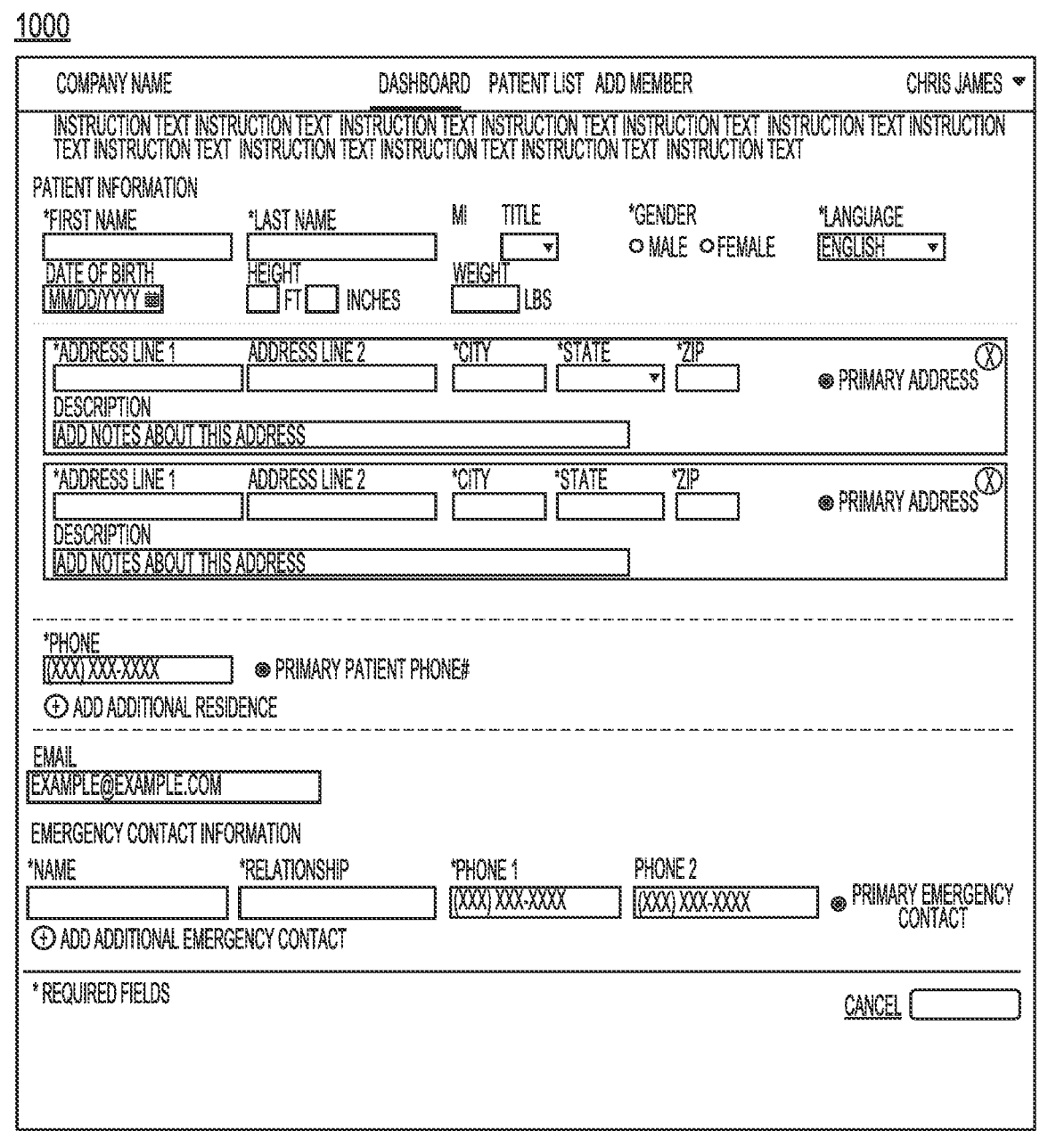

FIG. 10 is a screenshot 1000 illustrating features that may allow a practitioner to request enrollment for a patient in remote patient management, as previously described. A practitioner may further view a list of all enrolled patients, as illustrated in the screenshot 1100. In contrast to the screenshot 500 of FIG. 5, the list may display provider names, insurance IDs, medical IDs, times at which patients were last contacted, and statuses of patients. This list of patients may be searched and/or filtered. An example search is illustrated in the screenshot 1200 of FIG. 12. Searches may be performed based on any number of parameters including but not limited to patient division, insurance, condition, suspension, and measurement holds.

Figure 13:
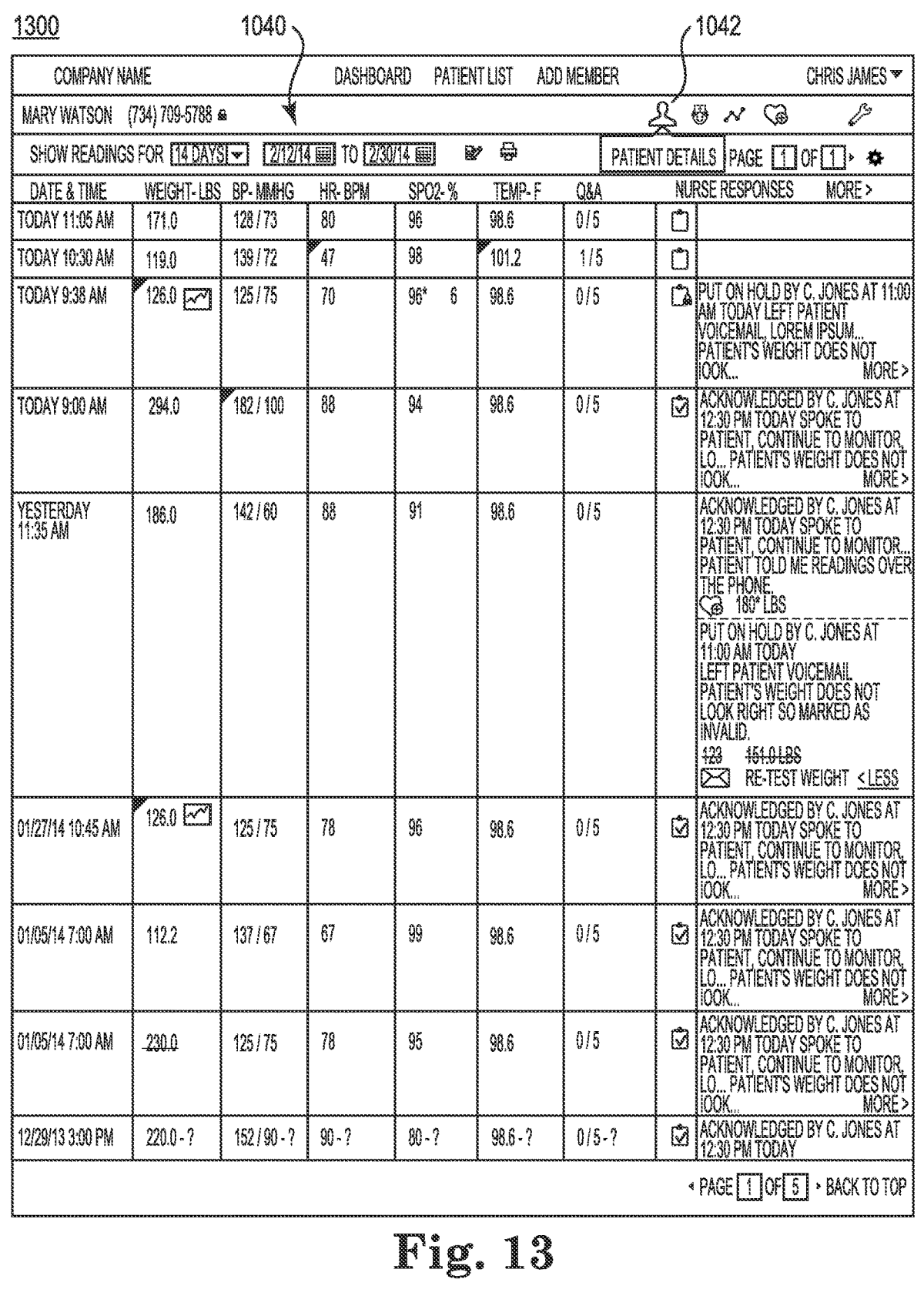

FIG. 13 is a screenshot 1300 illustrating a patient homepage for a particular patient enrolled in remote patient management. As illustrated, the patient homepage may display medical history of the patient, including previous measurements and notes provided by the practitioner. In some examples, the period over which medical history is displayed may be adjusted using date fields 1040.

In some examples, selecting a particular icon of the patient homepage may provide additional functionality. For example, selecting a patient details icon may provide a practitioner with more information regarding a patient. With reference to the screenshot 1400 of FIG. 14, selecting the patient details icon may display a patient sub-menu 1043 including selectable icons for patient information, medications, clinical orders, account history, alert history, patient management, patient assignment, and account status. Selecting one of the sub-menu icons may display the additional information regarding the patient. By way of example, selecting a patient information icon may display additional patient information as illustrated in the screenshot 1500 of FIG. 15.

In another example, selecting a clinician notes icon may allow a practitioner to provide notes regarding the patient. With reference to the screenshot 1600 of FIG. 16, selecting a patient information icon 1044 may open a window in which clinician notes may be provided and/or stored.

In yet another example, selecting a trends icon may allow a practitioner to review measurements plotted graphically. With reference to the screenshot 1700 of FIG. 17, selecting a trend icon 1048 may allow a practitioner to select trends corresponding to any number of vitals measured using measurement devices 106 associated with the patient or corresponding to information entered by the patient such as answers to a series of questions answered on a periodic (e.g., daily) basis. By way of example, a practitioner may select a trend 1050 for weight measurements, trend 1052 for blood pressure measurements, trend 1054 for heart rate measurements, trend 1056 for blood oxygen measurements, trend 1058 for temperature measurements, and trend 1060 for answers to questions provided by the practitioner to the patient. It will be appreciated that in other examples trends for additional vitals and/or patient inputs may be selected as well.

In yet another example, selecting a manual entry icon may allow a practitioner to enter vitals for a patient manually. With reference to the screenshot 1800 of FIG. 18, selecting a manual entry icon 1062 may open a vitals window 1063 in which a practitioner may enter measurements for one or more vitals manually. In some embodiments, a practitioner may further erase and/or modify one or more measurements.

In yet another example, selecting a patient message icon may allow a practitioner to provide a message to a patient. With reference to the screenshot 1900 of FIG. 19, selecting a message icon 1064 may open a message window 1065 in which a practitioner may provide a message to the patient.

In yet another example, selecting a settings icon may allow a practitioner to adjust various settings associated with a patient. With reference to the screenshot 2000 of FIG. 20, a practitioner may select a test schedule icon 1068 in a submenu of a settings icon 1066. Selecting the test schedule icon 1068 in this manner may allow a practitioner to select which vitals of a patient are to be measured by a patient, when and how often the vitals are to be measured, and/or which questions to ask the patient. With reference to the screenshot 2100 of FIG. 21, a practitioner may select a parameters icon 1070 to adjust preferred ranges for vitals and/or conditions for alerts.

FIGS. 22-25 are various screenshots of a GUI for facilitating remote patient management according to an embodiment of the present disclosure. The GUI described herein with reference to FIGS. 22-25 may correspond to a GUI utilized by local practitioner devices 160. It will be appreciated by those having skill in the art that any and all patient information provided in FIGS. 22-25 is provided for the purposes of illustration only and in no way comprises actual patient information.

FIG. 22 is a screenshot 2200 of a GUI that may be used to manage one or more patients enrolled in remote patient management. In some examples, the GUI may be displayed in response to a practitioner being authenticated with the healthcare management engine. In other examples, no authentication may be required by the healthcare management engine. As illustrated in the screenshot 2200, a list of patients and various vitals for each patient may be viewed simultaneously. Additionally, a last practitioner to view medical history for each patient may be displayed as well.

In instances in which a practitioner desires to view medical history of a patient, a practitioner may select the desired patient from the list presented in the screenshot 2200. With reference to the screenshot of 2300 of FIG. 23, selecting a patient may present a patient homepage for the selected patient. The patient homepage may display medical history of the patient, including previous measurements and answers provided by the patient to one or more questions. In some examples, the period over which medical history is displayed may be adjusted.

As previously described, health measurement devices 106 may be assigned to a particular patient such that the patient may use only those health measurement devices 106 as part of remote patient management of the patient. Moreover, in some cases, a user device 102 may be assigned to a patient. Accordingly, with reference to the screenshot 2400 of FIG. 24, in some examples a practitioner may assign a user device 102 (e.g., tablet) to a patient, for instance, using a serial number of the user device 102. As a result, the patient may provide measurements and other feedback to the healthcare management engine using only the user device 102 provided to and associated with the patient. Further, with reference to the screenshot 2500 of FIG. 25, a practitioner may assign one or more health measurement devices 106 to a patient, for instance, using a model number, ID number, and/or serial number. A practitioner may further select the units for one or more measurement types (e.g., Celsius or Fahrenheit for temperature measurements) and any questions that the practitioner prefers a patient answer during remote patient management. While fields for entering equipment information is illustrated for only one health measurement device 106 (e.g., blood oxygen monitor), it will be appreciated that fields any number of health measurement devices 106 may be provided such that any number of health measurement devices 106 may be associated with a patient.

While the screenshot 2400 of FIG. 24 and screenshot 2500 of FIG. 25 are described with respect to a practitioner assigning health measurement devices 106 to a patient, it will be appreciated that in some examples, healthcare measurement devices 106 may be automatically assigned to a patient by the healthcare management engine. For example, as described a third party server 170 may provide equipment information to the healthcare management engine. In response to receipt of the equipment information, the healthcare management engine may automatically assign health measurement devices 106 to the patient. Thereafter, a practitioner may edit the assignment of health measurement devices 106 as desired.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A computer hardware system comprising at least one processing unit coupled to a memory, wherein the memory is encoded with computer executable instructions that when executed cause the at least one processing unit to:
   receive, from a practitioner device, an enrollment request to enroll an existing patient in remote patient management, wherein the enrollment request includes vitals of the existing patient to be measured and a manner in which the vitals are to be measured including a measurement schedule, wherein the existing patient is remotely located from a medical facility;
   identify the vitals of the existing patient to be measured and the manner in which the vitals are to be measured based on the enrollment request;
   in response to receipt of the enrollment request, automatically provide an equipment request indicating the vitals of the existing patient to be measured and the manner in which the vitals are to be measured, wherein one or more health measurement devices and a user device are selected and caused to be provided to the existing patient in response to the equipment request, wherein the one or more health measurement devices are communicably coupled to the user device and the one or more health measurement devices are distinct from the user device;
   receive first equipment information corresponding to the user device and to the one or more health measurement devices for measuring the vitals of the existing patient, wherein the first equipment information corresponds to the one or more health measurement devices provided to the existing patient, and wherein the first equipment information includes a serial number, a model number, an identification number, a version number, or a combination thereof of the one or more health measurement devices provided to the existing patient;
   associate the existing patient with the first equipment information corresponding to the user device and the one or more health measurement devices;
   receive second equipment information from the user device, wherein the second equipment information corresponds to one or more health measurement devices for detecting one or more measurements, and wherein the second equipment information includes a serial number, a model number, an identification number, a version number, or a combination thereof of the one or more health measurement devices for detecting the one or more measurements;
   authenticate the user device in response to detection of a match between the first equipment information and the second equipment information;
   in response to the authentication of the user device, receive and store the one or more measurements from the one or more health measurement devices via the user device in a record corresponding to the existing patient, wherein the one or more measurements include the vitals to be measured; and
   in response to a failure to authenticate the user device, receive none of the one or more measurements from the one or more health measurement devices.

2. The computer hardware system of claim 1, wherein the one or more health measurement devices provided to the existing patient includes at least one of a scale, a glucose monitor, an oxygen monitor, a blood pressure monitor, a thermometer, or a heart rate monitor.

3. The computer hardware system of claim 1, wherein the computer executable instructions, when executed, cause the at least one processing unit to provide an equipment request indicating the vitals of the existing patient to be measured include instructions that when executed cause the at least one processing unit to provide an equipment request to a third party server.

4. The computer hardware system of claim 1, wherein the computer executable instructions, when executed, cause the at least one processing unit to:
   provide an account for the existing patient responsive to receipt of the enrollment request.

5. The computer hardware system of claim 1, wherein the computer executable instructions, when executed, cause the at least one processing unit to:
   identify the one or more health measurement devices provided to the existing patient based on the vitals of the existing patient to be measured.

6. The computer hardware system of claim 1, wherein the computer executable instructions, when executed, cause the at least one processing unit to:
   authenticate a practitioner device.

7. The computer hardware system of claim 1, wherein the computer executable instructions, when executed, cause the at least one processing unit to:
   receive a measurement from the user device associated with the existing patient; and
   determine whether the measurement was provided by the one or more health measurement devices provided to the existing patient.

8. The computer hardware system of claim 7, wherein the computer executable instructions, when executed, cause the at least one processing unit to:
   determine whether the measurement is within a range.

9. A method, comprising:
receiving, at a third party server, an equipment request from a healthcare management system server via a network, wherein the equipment request includes vitals of an existing patient enrolled in remote patient management to be measured and a manner in which the vitals are to be measured including a measurement schedule, wherein the existing patient is remotely located from a medical facility;
identifying, at the third party server, a plurality of health measurement devices based on the vitals of the existing patient to be measured and the manner in which the vitals are to be measured; and
in response to identifying the plurality of health measurement devices:
   providing, from the third party server, respective equipment information corresponding to each of the plurality of health measurement devices to the healthcare management system server via the network, wherein the respective equipment information for each of the plurality of health measurement devices includes a serial number, a model number, an identification number, a version number, or a combination thereof for each of the plurality of health measurement devices; and
   causing, by the third party server, the plurality of health measurement devices and a user device to be provided to the existing patient in response to the equipment request and identification of the plurality of health measurement devices, wherein the healthcare management system server associates the existing patient with the plurality of health measurement devices, wherein the healthcare management system server is configured to authenticate the user device in response to detection of a match between the equipment information of at least one of the plurality of health measurement devices provided from the third party server and one or more health measurement devices for detecting one or more measurements, and wherein the plurality of health measurement devices are communicably coupled to the user device and the plurality of health measurement devices are distinct from the user device.

10. The method of claim 9, further comprising:
prior to causing the plurality of health measurement devices and the user device to be provided to the existing patient, configuring the user device to communicate with the plurality of health measurement devices.

* * * * *